United States Patent
Rehman et al.

(10) Patent No.: US 9,232,977 B1
(45) Date of Patent: Jan. 12, 2016

(54) INSTRUMENT GUIDING DEVICE

(76) Inventors: Tausif-Ur Rehman, Albuquerque, NM (US); Atiq-Ur Rehman, Albuquerque, NM (US); Gary Reynolds, Tucson, AZ (US)

(*) Notice: Subject to any disclaimer, the term of this patent is extended or adjusted under 35 U.S.C. 154(b) by 843 days.

(21) Appl. No.: 12/732,796

(22) Filed: Mar. 26, 2010

Related U.S. Application Data

(60) Provisional application No. 61/164,322, filed on Mar. 27, 2009.

(51) Int. Cl.
*A61B 19/00* (2006.01)
*A61B 17/34* (2006.01)

(52) U.S. Cl.
CPC ....... *A61B 19/201* (2013.01); *A61B 2017/3407* (2013.01)

(58) Field of Classification Search
CPC .... A61B 19/201; A61B 19/20; A61B 19/203; A61B 2019/207; A61B 2019/208; A61B 2017/3407; A61B 19/22; B25J 9/047; B25J 9/048; Y10T 4/20201
USPC .................................. 606/130; 600/417, 429
See application file for complete search history.

(56) References Cited

U.S. PATENT DOCUMENTS

| | | | | |
|---|---|---|---|---|
| 1,093,112 A | * | 4/1914 | Clarke | 600/587 |
| 1,129,333 A | * | 2/1915 | Clarke | 600/587 |
| 2,697,433 A | * | 12/1954 | Zehnder | 606/96 |
| 3,016,899 A | * | 1/1962 | Stenvall | 604/175 |
| 3,115,140 A | * | 12/1963 | Volkman | 607/116 |
| 3,135,263 A | * | 6/1964 | Connelley, Jr. | 606/129 |
| 3,262,452 A | * | 7/1966 | Hardy et al. | 606/130 |
| 3,941,127 A | * | 3/1976 | Froning | 604/506 |
| 4,613,324 A | * | 9/1986 | Ghajar | 604/539 |
| 4,638,798 A | * | 1/1987 | Shelden et al. | 606/130 |
| 4,706,665 A | * | 11/1987 | Gouda | 606/130 |
| 4,722,331 A | * | 2/1988 | Fox | 606/96 |
| 4,733,661 A | * | 3/1988 | Palestrant | 606/108 |
| 4,841,967 A | * | 6/1989 | Chang et al. | 606/130 |
| 4,883,053 A | * | 11/1989 | Simon | 606/130 |
| 4,931,056 A | * | 6/1990 | Ghajar et al. | 606/130 |
| 4,955,891 A | * | 9/1990 | Carol | 606/130 |
| 4,998,938 A | * | 3/1991 | Ghajar et al. | 606/130 |
| 5,094,243 A | * | 3/1992 | Puy et al. | 600/459 |
| 5,102,391 A | * | 4/1992 | Palestrant | 604/116 |
| 5,201,742 A | * | 4/1993 | Hasson | 606/130 |
| 5,242,455 A | * | 9/1993 | Skeens et al. | 606/130 |
| 5,246,448 A | * | 9/1993 | Chang | 606/130 |
| 5,452,720 A | * | 9/1995 | Smith et al. | 600/427 |
| 5,891,034 A | * | 4/1999 | Bucholz | 600/426 |
| 5,891,158 A | * | 4/1999 | Manwaring et al. | 606/130 |
| 6,132,437 A | * | 10/2000 | Omurtag et al. | 606/130 |

(Continued)

*Primary Examiner* — David C Eastwood
*Assistant Examiner* — Erin Colello

(57) ABSTRACT

An instrument guiding device featuring a base having an aperture for a catheter; one or more legs disposed on the base; a first plate and a second plate each extending upwardly from the base perpendicularly to each other, the second plate is pivotally attached to the base; a guide component having an inner channel adapted to receive the catheter, the first end of the guide component is pivotally attached to the second plate, the guide component can be pivoted toward sides of the second plate; a first scale disposed on the first plate, a second scale disposed on the second plate; reference markers on the second plate and on the guide component; and a temporary attachment means for holding the second plate in place with respect to the first plate and for holding the guide component in place with respect to the second plate.

10 Claims, 6 Drawing Sheets

(56) References Cited

U.S. PATENT DOCUMENTS

| | | | |
|---|---|---|---|
| 6,331,180 B1* | 12/2001 | Cosman et al. | 606/130 |
| 6,409,735 B1* | 6/2002 | Andre et al. | 606/130 |
| 6,799,074 B1* | 9/2004 | Thomas et al. | 607/116 |
| 6,949,105 B2* | 9/2005 | Bryan et al. | 606/130 |
| 6,966,876 B2* | 11/2005 | Irion et al. | 600/102 |
| 7,033,326 B1* | 4/2006 | Pianca et al. | 600/585 |
| 7,033,367 B2* | 4/2006 | Ghahremani et al. | 606/108 |
| 7,133,713 B2* | 11/2006 | Zan | 600/415 |
| 7,559,935 B2* | 7/2009 | Solar et al. | 606/130 |
| 7,636,596 B2* | 12/2009 | Solar | 600/429 |
| 7,651,506 B2* | 1/2010 | Bova et al. | 606/130 |
| 7,824,417 B2* | 11/2010 | Magnusson et al. | 606/130 |
| 8,491,603 B2* | 7/2013 | Yeung et al. | 606/130 |
| 2002/0161446 A1* | 10/2002 | Bryan et al. | 623/17.15 |
| 2003/0055436 A1* | 3/2003 | Daum et al. | 606/130 |
| 2003/0229338 A1* | 12/2003 | Irion et al. | 606/1 |
| 2004/0260312 A1* | 12/2004 | Magnusson et al. | 606/130 |
| 2005/0055035 A1* | 3/2005 | Cosman et al. | 606/130 |
| 2005/0085822 A1* | 4/2005 | Thornberry et al. | 606/86 |
| 2005/0216026 A1* | 9/2005 | Culbert | 606/96 |
| 2006/0229641 A1* | 10/2006 | Gupta et al. | 606/130 |
| 2007/0250078 A1* | 10/2007 | Stuart | 606/130 |
| 2007/0287910 A1* | 12/2007 | Stallings et al. | 600/426 |
| 2008/0183191 A1* | 7/2008 | Schoepp | 606/130 |
| 2008/0269777 A1* | 10/2008 | Appenrodt et al. | 606/130 |
| 2009/0000626 A1* | 1/2009 | Quaid et al. | 128/898 |
| 2009/0082783 A1* | 3/2009 | Piferi | 606/130 |
| 2009/0171203 A1* | 7/2009 | Avital et al. | 600/439 |
| 2009/0234369 A1* | 9/2009 | Bax et al. | 606/130 |
| 2009/0306499 A1* | 12/2009 | Van Vorhis et al. | 600/426 |

\* cited by examiner

INSTRUMENT GUIDING DEVICE

CROSS REFERENCE

This application claims priority to U.S. provisional application Ser. No. 61/164,322 filed Mar. 27, 2009, the specification of which is incorporated herein by reference in its entirety.

FIELD OF THE INVENTION

The present invention is directed to a device for helping guide an instrument (e.g., a surgical instrument, a catheter) into a brain, more particularly to a device for guiding the insertion of a catheter into a brain ventricle.

BACKGROUND OF THE INVENTION

A ventriculostomy is the insertion of a catheter into a ventricle of the brain. They are generally performed to monitor and/or manage intracranial pressure, to obtain cerebrospinal fluid (CSF) specimens, and/or to administer medications into the nervous system.

An example of a procedure for performing a ventriculostomy may include creating a burr hole in the skull (e.g., 11 cm above the nasion and 3 cm lateral of the midline), opening the dura, introducing a catheter with a stiffening stylet through the burr hole, and advancing the catheter freehand using external landmarks as a guide. If the procedure is successful, the CSF should flow. If the procedure is unsuccessfully, the catheter must be removed and the procedure attempted again using a modified trajectory. The present invention features an instrument guiding device that may be used to help insert a catheter into the brain ventricle.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

The present invention features an instrument guiding device for helping insert a surgical instrument such as a catheter into a brain ventricle. Without wishing to limit the present invention to any theory or mechanism, it is believed that the instrument guiding device of the present invention is advantageous over freehand techniques and/or other catheter positioning devices. It is believed that the present invention can help reduce the number of unsuccessful catheter placements and can help provide guidance for subsequent attempts if the placement is not successful. It is also believed that the instrument guiding device of the present invention may help eliminate some of the problems, inaccuracies, and risks associated with freehand catheter placement.

The instrument guiding device 100 of the present invention is not limited to use with surgical instruments, particularly catheters. The device 100 may be used in combination with monitors, endoscopes, needles (e.g., biopsy needles), forceps, suction devices, probes, or any other instrument. The instrument guiding device 100 is not limited to use in a ventriculostomy. A ventriculostomy is only one of many procedures with which this device 100 may be used.

In some embodiments, the instrument guiding device allows for setting a predetermined angle of entry for the catheter. In some embodiments, the instrument guiding device allows for a numeric adjustment to a trajectory angle upon a failed insertion attempt.

Figure 1:
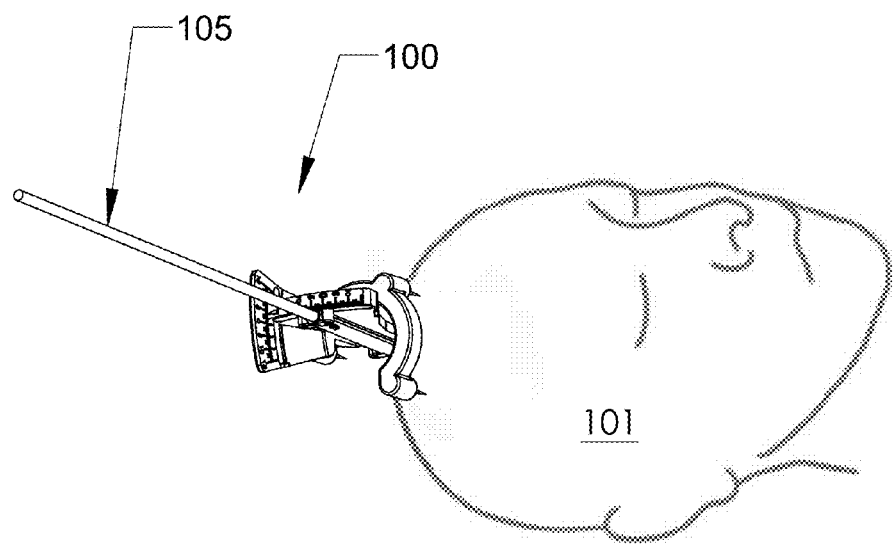
FIG. 1 is an in-use view of an embodiment of the device of the present invention as used on a patient's skull.
Figure 2:
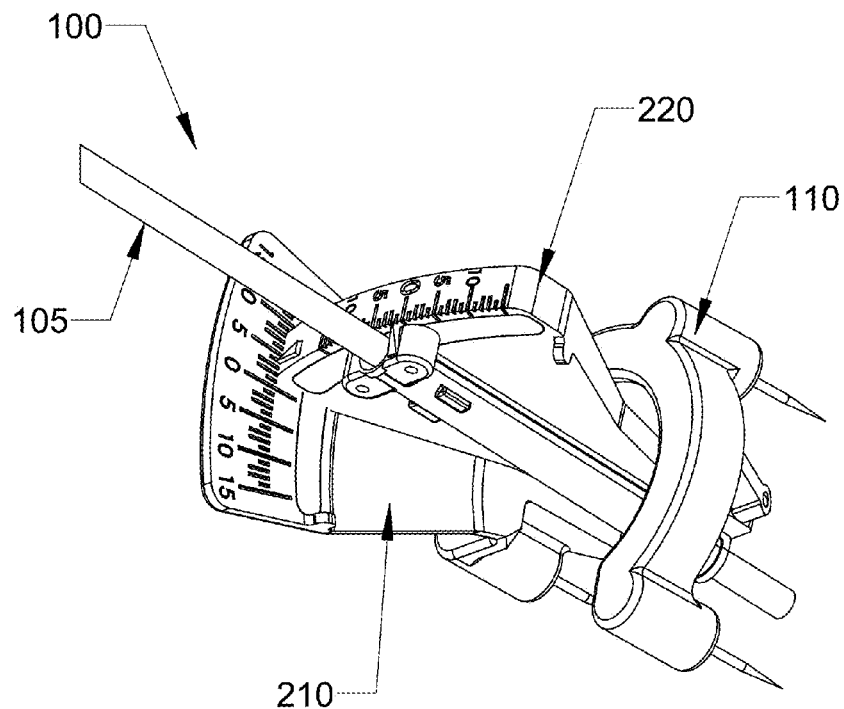
FIG. 2 is a first perspective view of the device of FIG. 1.
Figure 4:
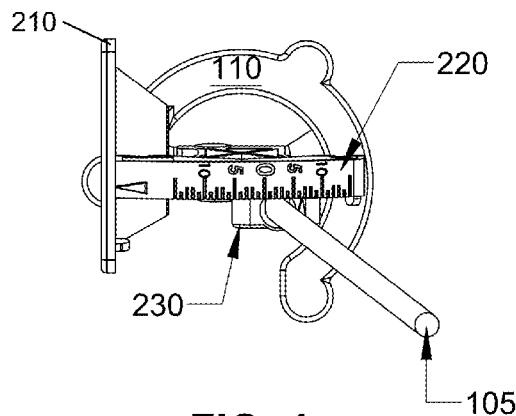
FIG. 4 is a top view of the device of FIG. 2.

Referring now to FIG. 1, the instrument guiding device 100 is for placing on the skull 101 of the patient. The device 100 is used during a procedure such as a ventriculostomy to guide a catheter 105 through the cranial surface into a ventricle of the brain. Generally, the instrument guiding device 100 is placed over a burr hole and rests on the skull 101. The catheter 105 can be inserted through the burr hole and advanced into the ventricle with the trajectory being directed by the guide device 100. Catheters used for these procedures are well known to one of ordinary skill in the art.

Referring now to FIG. 2-6, in some embodiments, the instrument guiding device 100 comprises a base platform 110. The base platform 110 may be generally flat. The base platform 110 may have a top surface 115 and a bottom surface 116. In some embodiments, the base platform 110 has an aperture through which a catheter 105 may pass.

The instrument guiding device 100 may comprise one or more legs 120. The legs may be disposed on the bottom surface 116 of the base platform 110. For example, in some embodiments, the instrument guiding device 100 comprises three legs 120. The instrument guiding device 100 is not limited to three legs 120.

Extending upwardly from the base platform 110 (e.g., upwardly from the top surface 115) is a first plate 210 and a second plate 220. In some embodiments, the first plate 210 corresponds generally to the sagittal plane and the second plate 220 corresponds generally to the coronal plane when the instrument guiding device 100 is placed on the skull 101.

The first plate 210 has a first side edge 211, a second side edge 212, a top edge 213, and a bottom edge. The second plate 220 has a first side edge 221, a second side edge 222, a top edge 223 and a bottom edge. The bottom edge of the first plate 210 is attached (e.g., removably attached) to the base platform 110. In some embodiments, the first plate 210 is generally stationary with respect to the base platform 110. The bottom edge of the second plate 220 is attached (e.g., removably attached) to the base platform 110. In some embodiments, the second plate 220 is pivotally attached to the base platform 110, for example the second plate 220 can pivot with respect to the base platform 110.

The first plate 210 and the second plate 220 are generally perpendicular to each other. For example, in some embodiments, the second side edge of the second plate 220 is slidably in contact (or near) with the front surface of the first plate 210.

The instrument guiding device 100 further comprises a guide component 230. In some embodiments, the guide component 230 is generally tubular having an inner channel 235 (e.g., lumen) connecting (e.g., fluidly connecting) the first end 231 to the second end 232 of the guide component 230. The inner channel 235 is adapted for receiving the catheter 105. The inner channel 235 is sufficiently large enough to allow passage of the catheter 105. The inner channel 235 may be limited in sizes so as to help minimize deviation from the intended trajectory (e.g., excess movement of the catheter 105 within the inner channel 235).

In some embodiments, the guide component 230 (e.g., the first end 231 of the guide component 230) is pivotally attached to the second plate 220 near the bottom edge. The guide component 230 can be pivoted toward the first side edge 221 and the second side edge 222 of the second plate 220 about a pivot point (e.g., the point at which the guide component 230 is attached to the second plate 220). In some embodiments, the guide component 230 slides over (or near) the front surface of the second plate 220 as it pivots.

Figure 3:
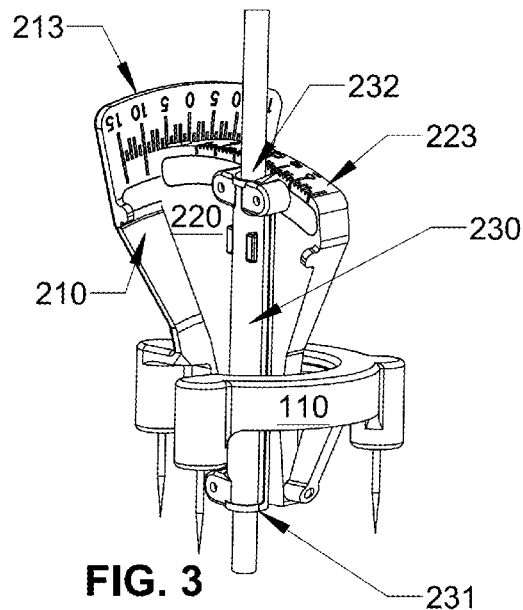
FIG. 3 is a second perspective view of the device of FIG. 2.
Figure 5:
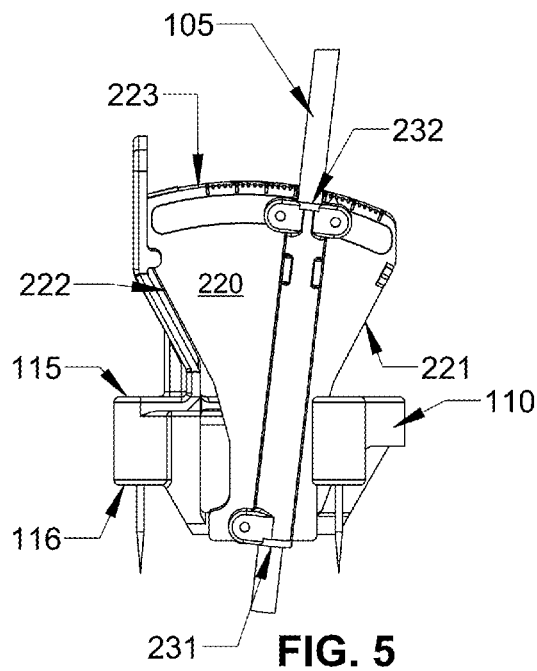
FIG. 5 is a first side view of the device of FIG. 2.
Figure 6:
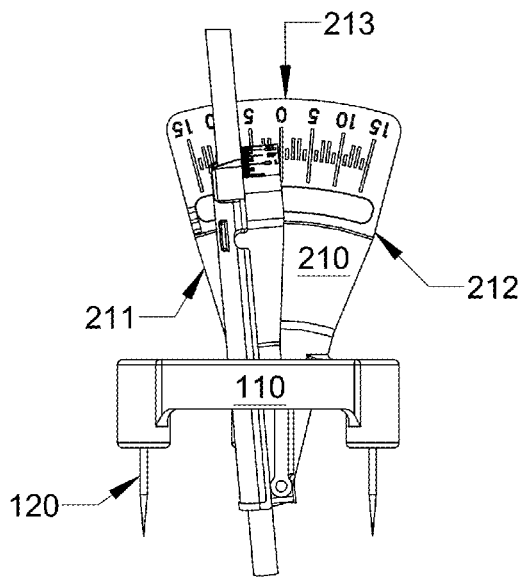
FIG. 6 is a second side view of the device of FIG. 2.

As shown in FIG. 3, in some embodiments, the second plate 220 is oriented at the aperture in the base platform 110. The guide component 230 may traverse the base platform 110 through the aperture.

Disposed near the top edge 213 of the first plate 210 is a plurality of graduated marks that forms a first scale. Disposed near the top edge 223 of the second plate 220 is a plurality of graduated marks that forms a second scale. In some embodiments, the scales may be marked with one degree graduations. In some embodiments, the scales may be marked with graduations of less than one degree (e.g., half degree graduations) or of more than one degree (e.g., two degree graduations). In some embodiments, the scale may cover a range of about 30 degrees, for example +15 degrees from a reference point and −15 degrees from the reference point. The scale may cover more or less than 30 degrees (e.g., +/−20 degrees, +/−30 degrees, etc.).

The guide device 100 of the present invention allows for a trajectory of the catheter to be chosen and implemented. The trajectory of the catheter 105 is generally determined from a first angle and a second angle. The first angle corresponds to the angle of the second plate 220 with respect to the first plate 210. The angle of the second plate 220 is indicated by where the second plate 220 aligns on the first scale of the first plate 210. For example, a reference marker on the second plate 220 aligns with a graduated mark on the first scale on the first plate 210. In some embodiments, the reference marker on the second plate 220 may be located near the second side edge 222. In some embodiments, the reference marker on the second plate 220 is located at or near the top edge 213.

The second angle corresponds to the angle of the guide component 230 with respect to the second plate 220. The angle of the guide component 230 is indicated by where the guide component 230 aligns on the second scale on the second plate 220. For example, a reference marker on the guide component 230 aligns with a graduated mark on the second scale of the second plate 220. In some embodiments, the reference marker on the guide component 230 is located at or near the second end 232 of the guide component 230.

The second plate 220 may be held in place (e.g., at the first angle) with respect to the first plate 210 and the guide component 230 may be held in place (e.g., at the second angle) with respect to the second plate 220 with a temporary attachment means. In some embodiments, the temporary attachment means includes friction mechanism, a magnet mechanism, a hook-and-loop fastener mechanism, an adhesive mechanism, a mechanical fastener (e.g., tightening a screw to hold the device at an angle), the like, or a combination thereof.

Figure 7:
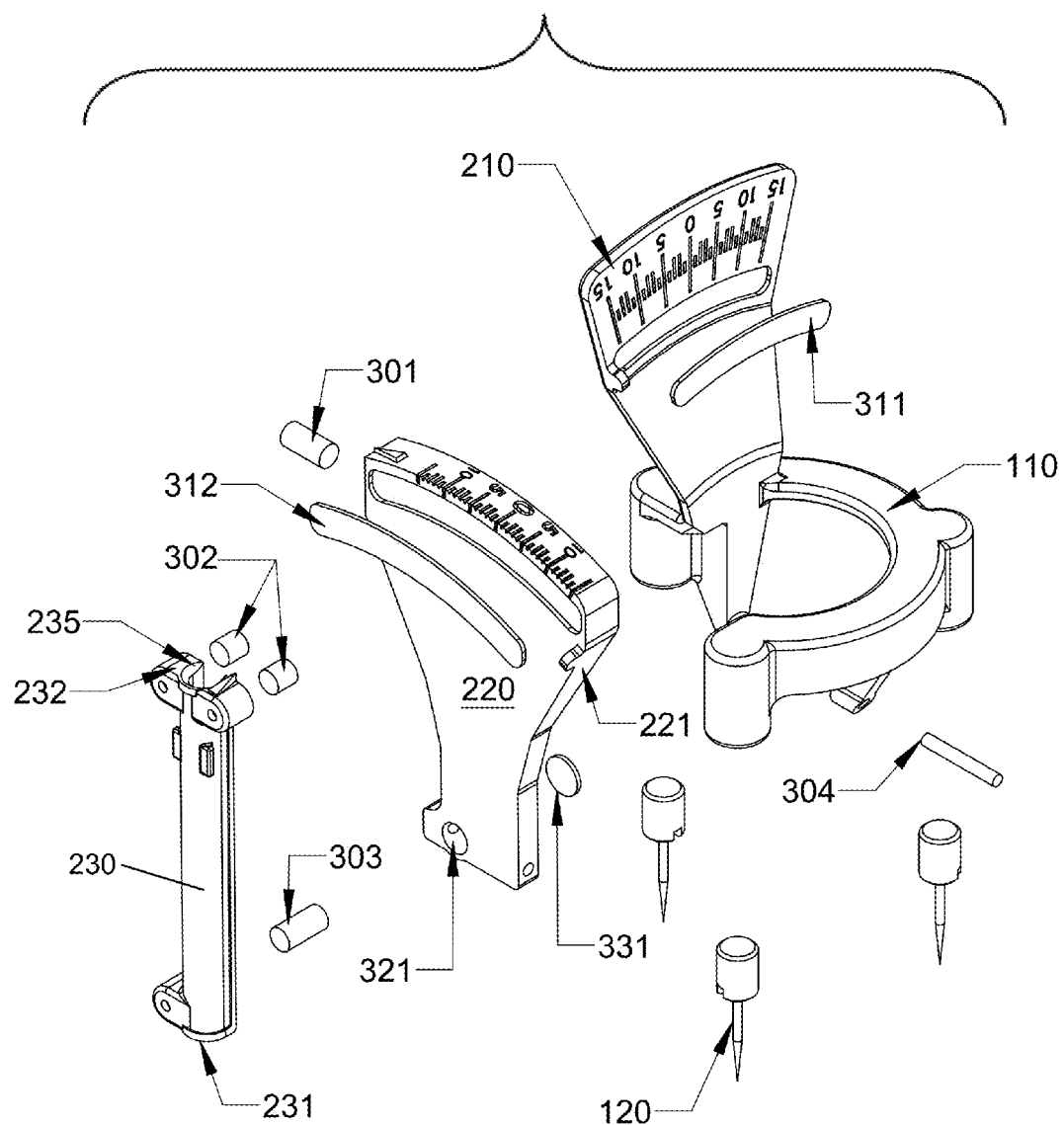
FIG. 7 is a first exploded view of the device of FIG. 2.
Figure 8:
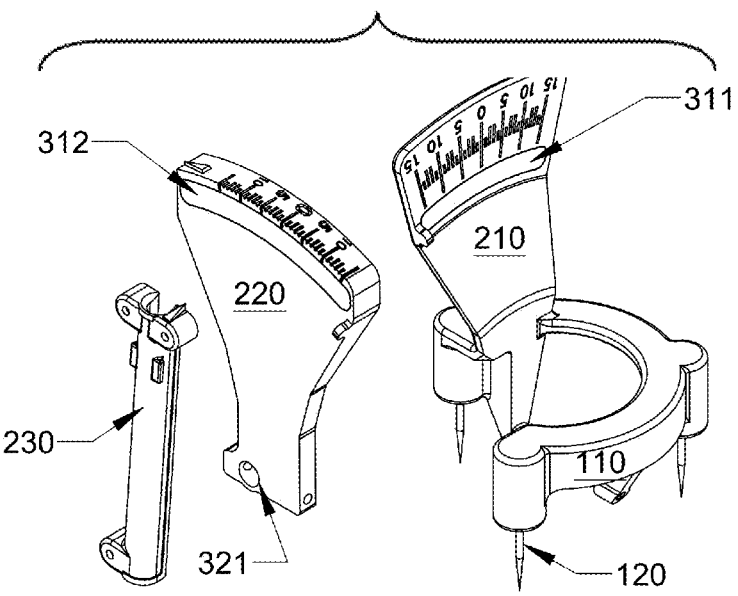
FIG. 8 is a second exploded view of the device of FIG. 2.
Figure 9:
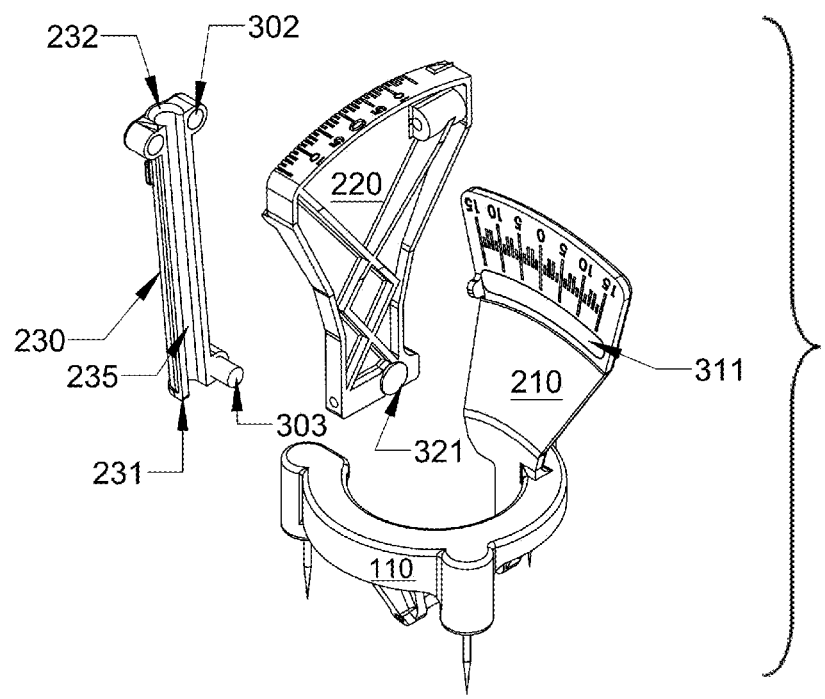
FIG. 9 is a third exploded view of the device of FIG. 2.

Referring now to FIG. 7-9, as an example, in some embodiments, a first magnet 301 is disposed in the second plate 220 (e.g., at the second side edge 222), and the first magnet 301 is attracted to a first metal (e.g., steel) insert 311 in the first plate 210. In some embodiments, a second magnet 302 is disposed in the guide component 230, and the second magnet 302 is attracted to a second metal (e.g., steel) insert 312 in the second plate 220. The second magnet 302 may be disposed in the guide component 230 near the second end 232. The first magnet 301 and second magnet 302 allow for manual pivoting of the second plate 220 and the guide component 230 to achieve the first and second angles, respectively. The guide component 230 and second plate 220 can be sufficiently held by friction created through the attraction of the magnets to the metal inserts. The temporary attachment means is not limited to these examples.

In some embodiments, the guide component 230 is pivotally attached to the second plate 220 via a third magnet 303. The third magnet 303 may be a cylindrical magnet residing in the guiding component 230. The third magnet 303 may extend through a first hole 321 in the second plate 220 and contact a first metal (e.g., steel) plate 331 on the back surface of the second plate 220. The first hole 321 is generally of sufficient size to allow rotation of the third magnet 303.

As shown in FIG. 7, in some embodiments, a pin 304 is pivotally disposed in a portion of the second plate 220, for example at the bottom edge of the second plate 220, and is pivotally disposed in a hole in the base platform 110. The pin 304 creates a pivot axis for the second plate 220 to pivot about the base platform 110. In some embodiments, the attachment of the first plate 210 to the base platform 110 may also axially retain the pivot pin 304.

Figure 10:
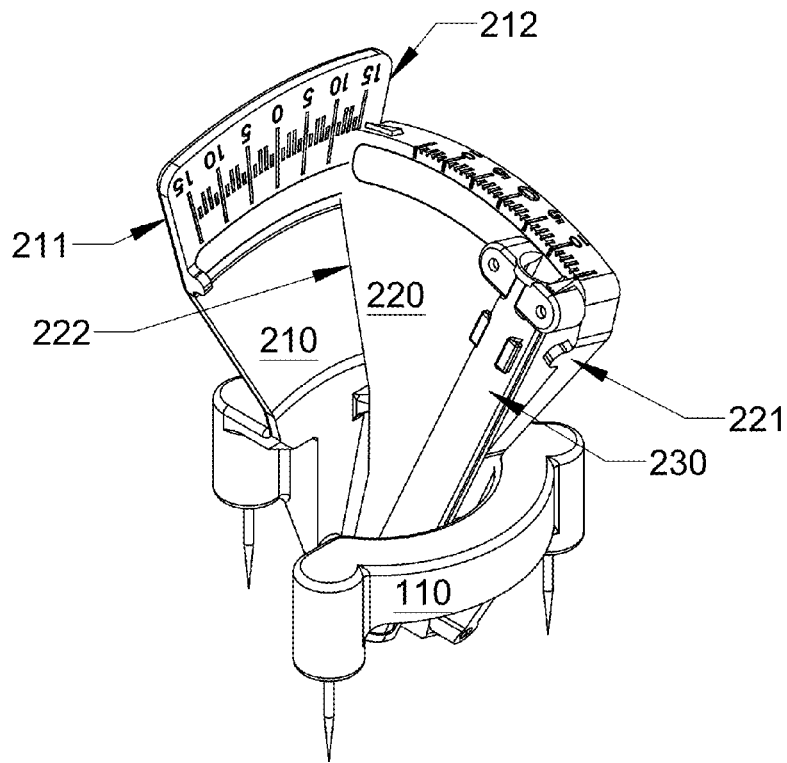
FIG. 10 is a third perspective view of the device of FIG. 2.
Figure 11:
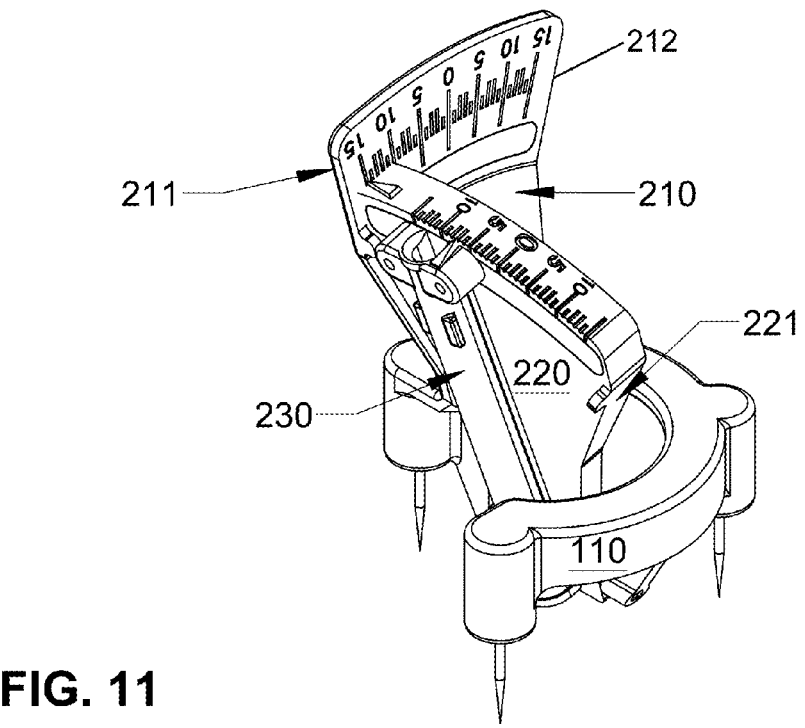
FIG. 11 is a fourth perspective view of the device of FIG. 2.
Figure 12:
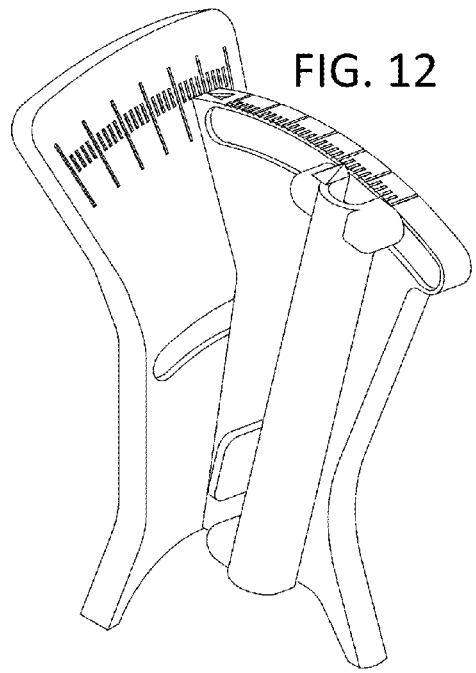
FIG. 12 is a perspective view of an alternative embodiment the device of the present invention.
Figure 13:
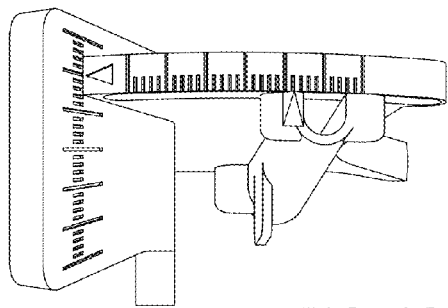
FIG. 13 is a top view of the device of FIG. 12.
Figure 14:
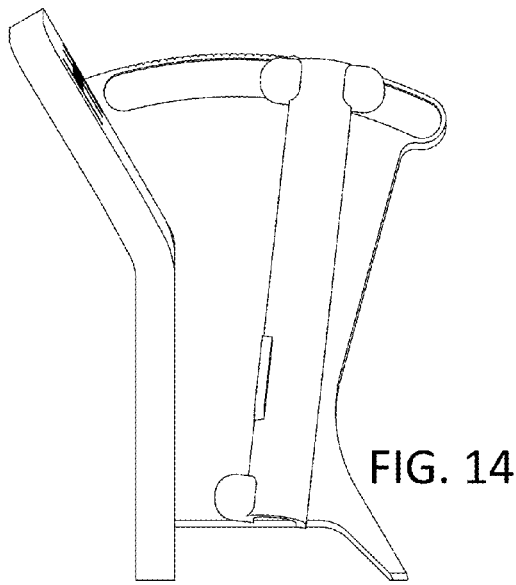
FIG. 14 is a first side view of the device of FIG. 12.
Figure 15:
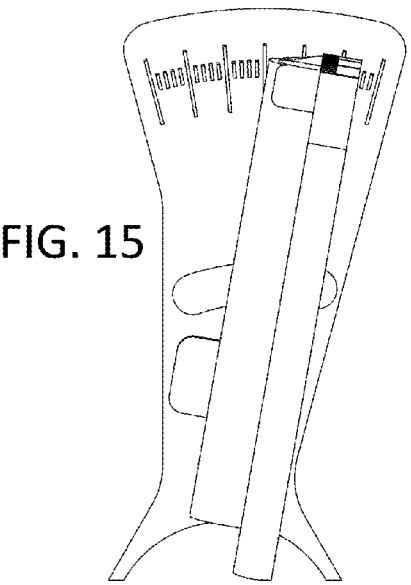
FIG. 15 is a second side view of the device of FIG. 12.

The second plate 220 and the guide component 230 can be manually pivoted to a desired position (e.g., the first and second angles). FIG. 10 shows the second plate 220 pivoted toward the second side edge 212 of the first plate 210 and the guide component 230 pivoted toward the first plate 210 (e.g., toward the second side edge 222 of the second plate 220). FIG. 11 shows the second plate 220 pivoted toward the first side edge 211 of the first plate 210 and the guide component pivoted toward the first side edge 221 of the second plate 220.

In some embodiments, the second plate 220 and the guide component 230 can be sufficiently held in place via friction created through the attraction of magnets to metal inserts. The present invention is not limited to this mechanism.

Referring now to FIG. 12-15, the instrument guiding device 100 of the present invention is not limited to the aforementioned embodiment. For example, in some embodiments, the instrument guiding device 100 does not have a stationary first plate 210 and a pivoting second plate 220 but has instead a pivoting first plate 210 and a stationary second plate 220. In some embodiments, the guide component 230 can pivot/slide on the first plate 210.

Spatial rotation can be decomposed into a combination of principle rotations. The instrument guiding device 100 of the present invention is not limited to the two specified axes of rotation described in the aforementioned embodiments. For example, if rotation about the x axis and y axis (e.g. rotation generally in the sagittal and coronal planes) is used to describe the aforementioned embodiment, rotation about the z axis could be used in combination with one or both of those axes to obtain an identical spatial trajectory.

FIGS. 12-15 illustrate an additional embodiment of the instrument guiding device 100 of the present invention. In some embodiments, the instrument guiding device 100 of the present invention does not include a base platform 110. In some embodiments, legs 120 are attached to the first plate 210 and/or second plate 220.

The instrument guiding device 100 of the present invention may be constructed from a variety of materials. For example, in some embodiments it may be advantageous if the instrument guiding device 100 is constructed from a rigid material. A rigid material may include a rigid plastic, steel, stainless steel, cast acrylic, the like, or a combination thereof. The instrument guiding device 100 may be constructed with injection molded materials. In some embodiments, the magnets are rare-earth neodymium permanent magnets or any other type of magnet. In some embodiments, the metal plates are constructed from a material comprising iron, such as low carbon steel. The plate may be covered with a coating (e.g., nickel coating). The construction of the instrument guiding device 100 is not limited to these materials.

The instrument guiding device 100 of the present invention may be constructed in a variety of sizes. Without wishing to limit the present invention to any theory or mechanism, it is believed that the height of the instrument guiding device 100 can correspond to the size of the scales (e.g., first scale, second scale) and/or can correspond to accuracy of the device.

In some embodiments, the inner channel 235 has a cross section that is U-shaped, circular, or of another shape. In some embodiments, the inner channel 235 has a diameter that is between about 2.0 to 3.0 mm. In some embodiments, the inner channel 325 has a diameter that is between about 3.0 and 4.0 mm (e.g., 3.5 mm). In some embodiments, the inner channel 235 has a diameter that is more than about 4.0 mm. The inner channel 325 is not limited to these dimensions.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. An instrument guiding device comprising:
   a base platform partially formed along a first axis and comprising an inner opening, wherein the inner opening is partially enclosed by the base platform and adapted to receive a medical tool;
   a plurality of legs, the legs configured to engage an outer surface of a skull;
   a first guide plate attached to the base platform and configured to provide guidance to an instrument guide component along a second axis; and
   a second guide plate removeably and pivotally attached to the base platform and configured to provide guidance to the instrument guide component along a third axis;
   the instrument guide component having an inner channel fluidly connecting a first end of the instrument guide component to a second end of the instrument guide component, wherein the first end of the guide component is pivotally attached to a bottom end of the second plate enabling the guide component to be selectively pivoted between a first side edge of the second plate and a second side edge of the second plate; and
   a first arcuate insert disposed on a surface of the first plate;
   a magnetic attachment element disposed on the first side edge of the second plate, the magnetic attachment element configured to removeably and magnetically attach to the first insert of the first plate at a user-selected position along the first insert;
   a second arcuate insert disposed on an instrument guide component facing surface of the second plate;
   wherein the first end of the guide component is pivotally and magnetically attached to the second plate using a second magnetic attachment element; and
   a third magnetic attachment element disposed proximate to the second end of the guide component and configured to magnetically engage the second insert at a user-selected position along the second insert.

2. The instrument guiding device of claim 1, wherein the second guide plate further comprises an aperture configured to receive a pin, and wherein the base platform further comprises a second aperture configured to receive the pin therethrough.

3. The instrument guiding device of claim 1, further comprising:
   a pin pivotally disposed in a recess of the second plate and in a recess of the base platform, the pin configured to pivotally engage the second plate to a user-selected point along the second axis of the first plate.

4. The instrument guiding device of claim 1, wherein the first and second axis are perpendicular.

5. An instrument guiding device comprising:
   a base platform partially formed along a first axis and comprising an inner opening, wherein the inner opening is partially enclosed by the base platform;
   a plurality of legs, the legs configured to engage an outer surface of a skull;
   a first guide plate removeably attached to the base platform and extending through the inner opening of the base platform and configured to provide guidance to an instrument along a second axis, wherein the first guide plate comprises an arcuate insert disposed along a radius from a rotation point; and
   a second guide plate removeably and rotatably attached to the base platform and extending through the inner opening of the base platform and configured to provide guidance to the instrument along a third axis, wherein the second plate comprises a magnetic attachment element configured to removeably and magnetically attach to the insert of the first plate.

6. The instrument guiding device of claim 5, wherein the second guide plate is rotatably attached to the base platform using a pin disposed in a recess of the second plate and in a recess of the base platform.

7. The instrument guiding device of claim 5, further comprising:
   an instrument guide component having an inner channel fluidly connecting a first end of the instrument guide component to a second end of the instrument guide component wherein the first end of the guide component is rotatably attached to a bottom end of the second plate enabling the guide component to be selectively rotated between a first side edge of the second plate and a second side edge of the second plate.

8. The instrument guiding device of claim 7, wherein the instrument guide component is magnetically attached to the second plate at a second rotation point.

9. The instrument guiding device of claim 8, wherein the instrument guide component further comprises a magnetic attachment element configured to selectively attach to the second plate along an insert, the insert disposed on the second plate at a radius from the second rotation point.

10. The instrument guiding device of claim 5, wherein each of the plurality of legs includes a needle at a distal end.

\* \* \* \* \*